(12) United States Patent
Myers et al.

(10) Patent No.: US 6,399,139 B2
(45) Date of Patent: *Jun. 4, 2002

(54) FOOD PRODUCTS HAVING ENHANCED COCOA POLYPHENOL CONTENT AND PROCESSES FOR PRODUCING THE SAME

(75) Inventors: Mary E. Myers, Lititz, PA (US); Chigozie V. Nwosu, Hackettstown, NJ (US); Eric J. Whitacre, Elizabethtown; John F. Hammerstone, Jr., Nazareth, both of PA (US)

(73) Assignee: Mars Incorporated, McLean, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/764,193

(22) Filed: Jan. 17, 2001

Related U.S. Application Data (63) Continuation of application No. 09/041,326, filed on Mar. 12, 1998, now Pat. No. 6,194,020, which is a continuation-in-part of application No. PCT/US97/15893, filed on Sep. 8, 1997, which is a continuation-in-part of application No. 08/709,406, filed on Sep. 6, 1996, now Pat. No. 6,015,913.

(51) Int. Cl.$^7$ .......................... A01N 65/00; A23L 1/28; A23G 1/02
(52) U.S. Cl. ............... 426/631; 426/542; 426/593; 549/386; 424/195.1
(58) Field of Search ............... 426/631, 542, 426/593, 479; 549/386; 424/195.1

(56) References Cited

U.S. PATENT DOCUMENTS

| | | | |
|---|---|---|---|
| 2,417,078 A | 3/1947 | Jones | 241/48 |
| 2,558,854 A | 7/1951 | Kempf et al. | 99/23 |
| 2,771,927 A | 11/1956 | Thaning | 146/227 |
| 3,904,777 A | 9/1975 | Goerling et al. | 426/631 |
| 3,923,847 A | 12/1975 | Roselius et al. | 260/412.8 |
| 3,955,489 A | 5/1976 | Goerling et al. | 99/483 |
| 3,997,680 A | 12/1976 | Chalin | 426/262 |
| 4,235,939 A | 11/1980 | Kimberely, Sr. | 426/549 |
| 4,271,754 A | 6/1981 | Homann | 100/37 |
| 4,322,444 A | 3/1982 | Zuilichem et al. | 426/241 |
| 4,435,436 A | 3/1984 | Terink et al. | 426/631 |
| 4,444,798 A | 4/1984 | Magnolato et al. | 426/422 |
| 4,701,337 A | 10/1987 | Frost et al. | 426/660 |
| 4,704,292 A | 11/1987 | Kattenberg | 426/565 |
| 4,758,444 A | 7/1988 | Terauchi et al. | 426/593 |
| 4,784,866 A | 11/1988 | Wissgott | 426/262 |
| 4,810,516 A | 3/1989 | Kong-Chan | 426/548 |
| 4,871,562 A | 10/1989 | Terauchi et al. | 426/330.3 |
| 4,999,197 A | 3/1991 | Wursch | 424/195.1 |
| 5,009,917 A | 4/1991 | Wiant et al. | 426/631 |
| 5,114,730 A | 5/1992 | Ellis | 426/593 |
| 5,244,099 A | 9/1993 | Zaltzman et al. | 209/466 |
| 5,252,349 A | 10/1993 | Carter, Jr. | 426/482 |
| 5,405,633 A | 4/1995 | Heidlas et al. | 426/442 |
| 5,464,649 A | 11/1995 | St. John et al. | 426/660 |
| 5,474,795 A | 12/1995 | Surber et al. | 426/660 |
| 5,554,645 A | 9/1996 | Romanczyk et al. | 514/456 |
| 5,709,903 A | 1/1998 | St. John et al. | 426/660 |
| 6,015,913 A * | 1/2000 | Kealey et al. | 549/386 |
| 6,194,020 B1 * | 2/2001 | Myers | 426/631 |

FOREIGN PATENT DOCUMENTS

| | | |
|---|---|---|
| GB | 1379116 | 1/1975 |
| WO | WO96/10404 | 4/1996 |
| WO | WO96/19923 | 7/1996 |
| WO | WO97/36597 | 1/1997 |

OTHER PUBLICATIONS

Beckett, S.T., Ed., "Industrial Chocolate Manufacture and Use", $2^{nd}$ Ed., Published by Blackie Academic Professional (an imprint of Chapman & Hall) Glasgow, U.K., 1994, by Chapman & Hall, pp. 55–82.

Minifie, Bernard W., Chocolate, Coca and Confectionery: Science and Technology, $3^{rd}$ Ed., Published by Chapman & Hall, Nw York, NY, 1989, by Van Nostrand Reinhold, pp. 31–51 and 61–76.

Swern, D., Ed., Bailey's Industrial Oil and Fat Products', $4^{th}$ Ed., John Wiley & Sons, New York, NY, (1982) vol. 2. pp. 175–251.

Wood, G.A.R., "Cocoa" $4^{th}$ Edition, Longman Scientific and Technical, Essex, England (1985), pp. 510–513.

Cook, L. Russell et al., "Chocolate Production and Use", Published by Harcourt Brace Jovanovich, Inc., New York, NY (1982), pp. 143–155 and 162–172.

\* cited by examiner

*Primary Examiner*—Carolyn Paden
(74) *Attorney, Agent, or Firm*—Margaret B. Kelley; Clifford Chance Rogers & Wells LLP (57) ABSTRACT

The invention provides food products, including confectioneries and chocolates, having conserved concentrations of polyphenols, and in particular cocoa polyphenols. The method of this invention avoids the significant and detrimental losses of polyphenols that occur during conventional manufacture by controlling the handling of ingredients in batching processing to provide a product having a significant amount of the cocoa polyphenol concentration present in the raw materials conserved in the finished product. Additionally, the production steps of milling/refining and conching may also be controlled and modified to provide the confectioneries of the present invention having conserved concentrations of cocoa polyphenols relative to the concentration of the polyphenols present in the starting ingredients. The cocoa polyphenol ingredient may be a cocoa ingredient, an extract of a cocoa ingredient (beans, liquor, or powder, etc.) or may be a synthesized derivative thereof, or may be a synthesized polyphenol compound or mixture of polyphenol compounds or derivative thereof.

20 Claims, 1 Drawing Sheet

FOOD PRODUCTS HAVING ENHANCED COCOA POLYPHENOL CONTENT AND PROCESSES FOR PRODUCING THE SAME

This application is a continuation of Ser. No. 09/041,326 filed Mar. 12, 1998, now U.S. Pat. No. 6,194,020, which is a continuation-in-part of PCT/US97/15893 filed Sep. 8, 1997 which published as WO 98/09533 on Mar. 12, 1998. The '893 PCT application is a continuation-in-part of Continued Prosecution Application Ser. No. 08/709,406 filed Sep. 6, 1996, which issued as U.S. Pat. No. 6,015,913 on Jan. 18, 2000.

BACKGROUND OF THE INVENTION

1. Field of the Invention

The invention relates to food products having a conserved or enhanced content of cocoa polyphenols and processes for producing the same. The food products prepared by the processes of this invention include edible food products, confectionery products and standard of identity and non-standard of identity chocolate products, and the like, having conserved concentrations of cocoa polyphenols therein.

2. Related Background Art

Polyphenolic compounds are bioactive substances that are derived from plant materials and are closedly associated with the sensory and nutritional quality of products derived from these plant materials. The term "cocoa polyphenol" includes the polyphenolic products, including proanthocyanidins, and more particularly procyanidins, extracted from cocoa beans and derivatives thereof. More specifically, the term "cocoa polyphenol" includes monomers of the formula $A_n$ (where n is 1) or oligomers of the formula $A_n$ (where n is an integer from 2 to 18, and higher), wherein A has the formula:

and R is 3-($\alpha$)-OH, 3-($\beta$)-OH, 3-($\alpha$)-O-saccharide, 3-($\beta$)-O-saccharide, 3-($\alpha$)-O-C(O)-R', or 3-($\beta$)-O-C(O)-R';

bonding between adjacent monomers takes place at positions 4, 6 or 8;

a bond to a monomer in positions 4 has alpha or beta stereochemistry;

X, Y and Z are selected from the group consisting of A, hydrogen, and a saccharide moiety, with the provisos that as to at least one terminal monomer, bonding of the adjacent monomer thereto is at position 4 and optionally Y=Z=hydrogen; and wherein the saccharide moiety is a mono- or di-saccharide moiety and may be optionally substituted with a phenolic moiety and r' may be an aryl or heteroaryl moiety optionally substituted with at least one hydroxyl group; and salts, derivatives and oxidation products thereof.

Advantageously, the saccharide moiety is derived from the group consisting of glucose, galactose, xylose, rhamnose and arabinose. The saccharide moiety and any or all of R, X, Y, and Z may optionally be substituted at any position with a phenolic moiety via an ester bond. The phenolic moiety is selected from the group consisting of caffeic, cinnamic, coumaric, ferulic, gallic, hydroxybenzoic and sinapic acids.

Many plant polypenols have antioxidant activity and have an inhibitory effect on mutagenesis and carcinogenesis. Cocoa polyphenol extracts, particularly procyanidine, have recently been shown to possess significant biological utility. Particularly, WO 97/36497 discloses that these extracts also function to reduce periodontal disease, atheroscleorsis and hypertension, inhibit LDL oxidation and DNA topoisomerase IT, modulate cyclo-oxygenase, lipoxygenase, nitric oxide or NO-synthease, apoptosis, platelet aggregation, and possess anti-inflammatory, antigingivitis and antiperiodontis activity. Moreover, WO-97/36497 discloses that oligomers 5–12 possess the highest anti-cancer activity of the polyphenolic compounds isolated from cocoa. Thus, consumption of these higher oligomers in cocoa products may provide significant health benefits. Accordingly, food products, such as confectioneries and cocoa-containing products (cocoa powders, chocolate liquors, or extracts thereof; having a high cocoa polyphenol concentration, especially a high concentration of cocoa polyphenol oligomers 5–12, would be especially desirable.

The cocoa polypenol extracts, or compounds further separated therefrom have generally been prepared, on a laboratory scale, by reducing cocoa beans to a powder, defatting the powder, and extracting and purifying the active compound(s) from the defatted powder. The powder is generally prepared by freeze-drying the cocoa beans and pulp, de-pulping and de-shelling the freeze-dried beans and grinding the de-shelled beans or nibs. The extraction of active compound(s) has been accomplished by solvent extraction techniques, and the extracts have been purified by gel permeation chromatography, preparative high performance liquid chromatography (HPLC) techniques, or by a combination of such methods, as disclosed in Romanczyk et al., U.S. Pat. No. 5,554,646.

Under-fermented and unfermented cocoa raw materials contain substantial amounts of cocoa polyphenols, compared to fermented cocoa. Fermentation and drying bring about complex changes in the cocoa bean, most notably, the formation of components required for the development of the characteristic flavor and color of cocoa. Fermentation, however, also significantly decreases the concentrations of polyphenolic compounds in the fermented cocoa beans, relative to the concentrations of polyphenolic compounds in unfermented or under-fermented beans. Traditional cocoa bean processing, including such steps as roasting or defatting of the cocoa beans, also reduces the cocoa polyphenol concentration in the cocoa powder or chocolate liquors produced thereby. Moreover, these processes reduce the concentrations of higher oligomeric polyphenols (oligomers 5–12) more rapidly than lower oligomers (2–4) or monomers. Accordingly, it was highly desirable to developments of conserving or retaining the higher oligomers that not only possessed more significant biological activity than lower oligomers, but also appeared to be more sensitive to processing conditions than the lower oligomers.

Accordingly, it would be highly desirable to develop processing techniques to prepare food products and confectioneries, particularly cocoa-containing confectioneries, that will conserve the cocoa polyphenol concentration of cocoa powders, chocolate liquors, or extracts thereof, in the finished, shelf-ready product.

SUMMARY OF THE INVENTION

The invention relates to novel food products, and their process of production, containing a conserved or enhanced concentration of polyphenols. In a preferred embodiment, the invention provides processes for producing confectionery products, including standard of identity and non-standard of identity chocolate products, having conserved concentrations of polypenols, and preferably cocoa polyphenols, and more preferably cocoa polyphenol oligomers. The process of the present invention comprises:

(a) mixing at least one ingredient of the product with at least one polypenol-conserving pre-treatment ingredient to form a mix, (b) combining the mix with at least one ingredient containing cocoa polyphenol, and (c) forming the polyphenol-containing product, wherein the product contains at least about 10% by weight more polyphenol than a product prepared without using the pre-treatment process according to step (a).

The process of this invention avoids the significant and detrimental losses of polyphenols that occur during conventional manufacture. This invention provides novel food products prepared from polyphenol-containing ingredients that may be cocoa ingredients, extracts of a cocoa material (beans, liquor, or powder, etc.) or may be a synthesized derivative thereof, or may be synthesized polyphenol compounds or a mixture of polyphenol compounds or derivative thereof. Mixing ingredients in a specific order provides a product having a significant amount of the cocoa polyphenol concentration, present in the raw materials, conserved in the finished product. Additionally, the production steps of milling/refining and conching may also be controlled and modified to provide the confectioneries of the present invention having conserved concentrations of cocoa polyphenols. Thus, the invention relates to processes of obtaining food products and confectioneries having a conserved concentration of cocoa polyphenols relative to the starting ingredients. The invention avoids the significant and detrimental losses of cocoa polyphenols that occur during conventional manufacture.

BRIEF DESCRIPTION OF THE DRAWINGS

FIGS. 1(a)–(d) illustrate the change in the surface of the cut bean half during the fermentation of the cocoa bean FIG. 1(a) depicts the cut bean of an unfermented cocoa bean; FIGS. 1(b)–(d) depict the cocoa bean as it is fermented, with FIG. 1(d) illustrating the fully fermented cocoa bean.

DETAILED DESCRIPTION OF THE INVENTION

It has now been determined that the retention of polyphenols, and particularly higher oligomeric (5–12) polyphenols, in food products is dependent upon the order of addition of ingredients during batch processing. Polyphenols are known to complex with proteins, alkaloids, metal cations and carbohydrates. Without being bound to theory, it is believed that the processes of this invention prevent or reduce the adverse interactions between the polyphenol-containing ingredients and the protein-containing and/or carbohydrate-containing ingredients used therein. The processes of the present invention provide finished, shelf-ready food products with conserved concentration of the cocoa polyphenols present in the polyphenol-containing ingredients used to prepare the food products. More preferably, the processes of the present invention provide finished, shelf-ready confectionary products with conserved concentration of cocoa polyphenol oligomers 5–12. The concentration of cocoa polyphenol pentamer (polyphenol oligomer 5), in the resulting products of the present invention, was used as an indicator of the effectiveness of cocoa polyphenol conservation in the processes of the invention.

The process of preparing a food product according to this invention comprises:

(a) mixing at least one ingredient of the product with at least one polyphenol-conserving pre-treatment ingredient to form a mix, (b) combining the mix with at least one ingredient containing cocoa polyphenol, and (c) forming the polyphenol-containing food product, wherein the product contains at least about 10% by weight more polyphenol than a product prepared without using the pre-treatment process according to step (a).

Additional ingredients desired in the resulting food product may be added at any point in the process.

As used herein, the term "food product" includes any edible product, including foods, confectioneries, and diet supplements, particularly cocoa-containing foods, confectioneries, and diet supplements. Confectioneries refer to any sweetened foods, particularly candy, chocolate, icings and the like.

The term "cocoa polyphenol" includes the procyanidins present in cocoa beans or a cocoa ingredient used in the production of confectionery products, chocolate confectioneries and chocolate products, extracts of cocoa beans or a cocoa ingredient comprising procyanidins, and synthesized derivatives thereof, and includes synthesized cocoa polyphenol compounds or synthesized mixtures of polyphenol compounds, and derivatives thereof. The term "cocoa ingredient" refers to a cocoa solids-containing material derived from shell-free cocoa nib and includes chocolate liquor and partially or fully defatted cocoa solids (e.g., cake or powder), alkalized cocoa powder or alkalized chocolate liquor and the like. The term "chocolate liquor" refers to the dark brown fluid "liquor" formed by grinding a cocoa nib. The fluidity is due to the breakdown of the cell walls and the release of the cocoa butter during the processing resulting in a suspension of ground particles of cocoa solids suspended in cocoa butter.

Preferred chocolate liquors include those from underfermented beans because the beans have a higher cocoa polyphenol content.

The cocoa polyphenol oligomers may be prepared by (a) protecting each phenolic hydroxyl group of a first and a second polyphenol monomer with a protecting group to produce a first and a second protected polyphenol monomer;

(b) functionalizing the 4-position of the first protected polyphenol monomer to produce a functionalized protected polyphenol monomer having the formula:

where c is 1 to 3, d is 1 to 4, y ti 2 to 6, R is a protecting group, and R' is H or OH;

(c) coupling the second protected polyphenol monomer with the functionalized protected polyphenol monomer to produce a protected polyphenol dimer;

(d) optionally repeating the protecting, functionalizing, and coupling steps to form polyphenol oligomers having a n monomeric units, where n is an integer from 3 to 18, preferably 5–12; and

(e) removing the protecting groups from the phenolic hydroxyl groups.

The preferred protected polyphenol monomer is a brominated protected epicatechin or brominated protected catechin, e.g., 6, 8, 6'-tribromo-epicatechin or a 6, 8, 6'-tribromo-catechin.

In the above process, the 4-position of the protected polyphenol monomer may be oxidatively functionalized using a quinone oxidizing agent in the presence of a diol, e.g., ethylene glycol, in which case y is 2.

The above process may further comprise the step of forming a derivative of the polyphenol oligomer by esterifying the polyphenol oligomer at the 3-position of at least one monomeric unit to produce an esterified polyphenol oligomer. The ester group may be selected from the group consisting of —OC(O)-aryl, —OC(O)-substituted aryl, —OC(O)-styryl, and OC(O)-substituted styryl, where the substituted aryl or substituted styryl group contains at least one substituent selected from the group consisting of halo, hydroxyl, nitro, cyano, amino, thiol, methylenedioxy, dihalomethylenedioxy, a $C_1$–$C_6$ alkyl, a $C_1$–$C_6$ alkoxy, a $C_1$–$C_6$ haloalkyl, a $C_1$–$C_6$ haloalkoxy, a $C_3$–$C_8$ cycloalkyl, and a $C_3$–$C_8$ cycloalkoxy. Preferably, the 3-position of at least one monomeric unit is converted to a derivative group derived from an acid selected from the group consisting of caffeic, cinnamic, coumaric, ferulic, gallic, hydroxybenzoic and simple acids.

The above process may further comprise the step of forming a derivative of the polyphenol oligomer by glycosylating the polyphenol oligomer at the 3-position of at least one monomeric unit to produce a glycosylated polyphenol oligomer. Preferably, the 3-position of at least one monomeric unit is converted to a derivative group selected from the group consisting of a —O-glycoside and an —O-substituted glycoside wherein the substituted glycoside is substituted by —C(O) aryl, —C(O)-substituted aryl, —C(O)-styryl, or —C(O)-substituted styryl groups. The substituted aryl or substituted styryl group may containing substituents selected from the group consisting of halo, hydroxyl, nitro, cyano, amino, thiol, methylenedioxy, dihalomethylenedioxy, a $C_1$–$C_6$ alkyl, a $C_1$–$C_6$ alkoxy, a $C_1$–$C_6$ haloalkyl, a $C_1$–$C_6$ haloalkoxy, a $C_3$–$C_8$ cycloalkyl and a $C_3$–$C_8$ cycloalkoxy. Preferably, the glycoside is derived from the group consisting of glucose, galactose, xylose, rhamnose, and arabinose structurally represented as oligomers of monomer A having the formula $A_n$, where n is 2–18, wherein A has the formula:

and R is 3-(α)-OH, 3-(β)-OH, 3-(α)-O-saccharide, 3-(β)-O-saccharide;

bonding between adjacent monomers takes place at positions 4, 6 or 8;

a bond to a monomer in position 4 has alpha or beta stereochemistry;

X, Y and Z are selected from the group consisting of A, hydrogen, and a saccharide moiety, with the provisos that as to at least one terminal monomer, bonding of the adjacent monomer thereto is at position 4 and optionally Y=Z=hydrogen; and salts thereof;

wherein the saccharide moiety is derived from a mono- or di-saccharide.

Synthesized derivatives of the cocoa polyphenols include compounds, according to the structure $A_n$, above, wherein R may be 3-(α)-O-saccharide, 3-(β)-O-saccharide, 3-(α)-O-C(O)-R', or 3-(β)-O-C(O)-R', wherein the saccharide moiety may be derived from a mono- or di-saccharide selected from the group consisting of glucose, galactose, xylose, rhamnose and arabinose; the saccharide moiety of any or all of R, X, Y, and Z may be optionally substituted at any position with a phenolic moiety via an ester bond; the phenolic moiety may be selected from the group consisting of caffeic, cinnamic, coumaric, ferulic, gallic, hydroxybenzoic and sinapic acids; and R' is an aryl or heteroaryl moiety optionally substituted with at least one hydroxy group. The substituted aryl or heteroaryl moiety of R' may preferably contain a substitution pattern corresponding to the substituted phenolic moieties of caffeic, cinnamic, coumaric, ferulic, gallic, hydroxybenzoic or sinapic acids.

Partially defatted cocoa solids having a high cocoa polyphenol (CP) content, i.e., a high cocoa procyanidin content, can be obtained by processing the cocoa beans directly to cocoa solids without a bean or nib roasting step. This method conserves the cocoa polyphenols because it omits the traditional roasting step. The method comprises the steps of: (a) heating the cocoa beans to an internal bean temperature just sufficient to reduce the moisture content to about 3% by weight and to loosen the cocoa shell; (b) winnowing the cocoa nibs from the cocoa shells; (c) screw pressing the cocoa nibs; and (d) recovering the cocoa butter and partially defatted cocoa solids which contain cocoa polyphenols including cocoa procyanidins.

Optionally, the cocoa beans are cleaned prior to the heating step, e.g., in an air fluidized bed density separator. The winnowing can also be carried out in a air fluidized bed density separator. Preferably, the cocoa beans are heated to an internal bean temperature of about 100° C. to about 110° C., more preferably less than about 105° C., typically using a infra red heating apparatus for about 3 to 4 minutes. If desired, the cocoa solids can be alkalized and/or be milled to a cocoa powder.

The internal bean temperature (IBT) can be measured by filling an insulated container such as a thermos bottle with beans (approximately 80–100 beans). The insulated container is then appropriately sealed in order to maintain the temperature of the sample therein. A thermometer is inserted into the bean-filled insulated container and the temperature of the thermometer is equilibrated with respect to the beans in the thermos. The temperature reading is the IBT temperature of the beans. IBT can also be considered the equilibrium mass temperature of the beans.

Cocoa beans can be divided into four categories based on their color: predominately brown (fully fermented), purple/brown, purple, and slaty (underfermented). Preferably, the cocoa solids are prepared from underfermented cocoa beans, i.e., slaty cocoa beans, purple cocoa beans, mixtures of slaty and purple cocoa beans, mixtures of purple and brown cocoa beams, or mixture of slaty, purple, and brown cocoa beans. More preferably, the cocoa beans are slay and/or purple cocoa beans which have a higher cocoa polyphenol content than fermented beans.

The cocoa polyphenols, including the cocoa procyanidins, may be solvent extracted from the partially defatted cocoa solids prepared from the unroasted cocoa beans. The cocoa procyanidine oligomers identified in the extract include the dimer to the nonamer.

The partially defatted cocoa solids and/or cocoa polyphenol extracts can be used in therapeutic compositions, optionally with a carrier or a diluent. The therapeutic compositions are useful as antineoplastic compositions, antioxidants, antimicrobial agents, nitric oxide (NO) or NO-synthase modulators, cyclo-oxygenase modulators, lipoxygenase modulators, and in vivo glucose modulators.

The cocoa polyphenol (CP) content, including the cocoa procyanidin content, is higher when underfermented cocoa beans or blends thereof a fermentation factor of 275 or less, are selected for processing into the cocoa components.

The "fermentation factor" is determined using a grading system for characterizing the fermentation of the cocoa beans. Slaty is designated 1, purple is 2, purple/brown is 3, and brown is 4. The percentage of beans falling within each category is multiplied by the weighted number. Thus, the "fermentation factor" for a sample of 100% brown beans would be 100×4 or 400, whereas for a 100% sample of purple beans it would be 100×2 or 200. A sample of 50% slaty beans and 50% purple beans would have a fermentation factor of 150 [(50×1)+(50×2)].

The high CP chocolate liquor and/or high CP cocoa solids are prepared by: (a) roasting the selected cocoa beans (fermentation factor of 275 or less) to an internal bean temperature of 95° C. to 160° C., (b) winnowing the cocoa nibs from the roasted cocoa beams, (c) milling the cocoa nibs into the chocolate liquor; and (d) optionally recovering cocoa butter and partially defatted cocoa solids from the chocolate liquor. Alternatively, the chocolate liquor and/or cocoa solids can be prepared by: (a) heating the selected cocoa beans (fermentation factor of 275 or less) to an internal bean temperature of 95–135° C. to loosen the cocoa shell from the cocoa nibs; (b) winnowing the cocoa nibs from the cocoa shells; (c) roasting the cocoa nibs to an internal nib temperature of 95° C. to 160° C.; (d) milling the roasted nibs into the chocolate liquor; and (e) optionally recovering cocoa butter and partially defatted cocoa solids from the chocolate liquor. Chocolate liquor and partially defatted cocoa solids containing at least 50,000 $\mu$g of total cocoa procyanidins and/or at least 5,000 $\mu$g of cocoa procyanidin pentamer per gram of nonfat cocoa solids can be prepared by the above processes.

An extract containing cocoa polyphenols including cocoa procyanidins can be prepared by solvent extracting the partially defatted cocoa solids or nonfat cocoa solids prepared from the roasted underfermented cocoa beans or cocoa nibs.

High CP food products may be prepared using the high CP roasted cocoa nibs, high CP chocolate liquors, and/or high CP partially defatted or nonfat cocoa solids. The food products include per food, dry cocoa mixes, puddings, syrups, cookies, savory sauces, rice mixes, and rice cakes. Preferably, the food products are confectioneries, e.g., a dark chocolate or a milk chocolate. The extract can also be used to prepare foods having high cocoa polyphenol contents.

The health of a mammal can be improved by administering to the mammal a composition containing cocoa procyanidins or the above high CP cocoa components. In these compositions the total amount of the cocoa procyanidin oligomers is at least 1 $\mu$g or greater and the composition is administered daily over greater than 60 days.

The food products of this invention may contain one or more of the cocoa polyphenol monomers, oligomers 2–18, or derivatives thereof. Preferably, the food products of this invention contain mixtures of cocoa polyphenol oligomers 2–18, or derivatives thereof; more preferably, the food products contain mixtures of cocoa polyphenol oligomers 5–12, or derivatives thereof.

The term "oligomer", as used herein, refers to any compound of the formula presented above, wherein n is 2 through 18, and preferably, wherein n is 5–12. When n is 2, the oligomer is termed a "dimer"; when n is 3, the oligomer is termed a "trimer"; when n is 4, the oligomer is termed a "tetramer"; when n is 5, the oligomer is termed a "pentamer"; and similar recitations may be designated for oligomers having n up to and including 18 and higher, such that when n is 18, the oligomer is termed an "octadecamer".

A "pre-treatment ingredient" is any ingredient that may be used in food products, confectionery products and/or chocolate products that functions to conserve and/or retain the cocoa polyphenol concentration of any cocoa polyphenol-containing ingredient used therein. Preferably, the pre-treatment ingredient is any ingredient that may be used in food products, especially confectionery products and/or chocolate products, that functions to conserve and/or retain the concentration of cocoa polyphenol oligomers 5–12 of any ingredient containing such oligomers. The pre-treatment ingredient demonstrates an activity that prevents reaction, complexation, decomposition or adverse interaction of cocoa polyphenols with any of the other ingredients or apparatus used in the preparation of such products or with any polyphenol reactive material generated from or by the other ingredients during the preparation of the products. An example of a reactive material that may be generated from or by other ingredients during the preparation of these food products is a free-radical reactive intermediate species. The pre-treatment ingredients may function to prevent the formation of polyphenol-reactive materials or interact with polyphenol-reactive materials, thereby preserving the cocoa-polyphenol concentration of the cocoa polyphenol-containing ingredient in the products. Exemplary pre-treatment ingredients that may be used in the food products of this invention include water, fats, emulsifying agents, cocoa ingredients, antioxidant compounds, flavoring agents, other polyphenol-containing ingredients, and the like.

The term "fat" as used herein, refers to triglycerides typically used in food products, especially confectionery products and chocolate products. Fats useful in this invention include the naturally occurring fats and oils such as cocoa butter, pressed cocoa butter, expeller cocoa butter, solvent extracted cocoa butter, refined cocoa butter, milk fat, anhydrous milk fat, fractionated milk fat, milk fat replacers, butterfact, fractionated butterfact, and other vegetable fact, as well as other modifications of these fats, including cocoa butter equivalents (CBE), cocoa butter substitutes (CBS), cocoa butter replacers (CBR), antiblooming agents, such as behenoyl oleoyl behenate (BOB), reduced calorie fats and/or synthetically modified fats, including reduced calorie fats and non-caloric fat substitutes. A reduced calorie fat is a fat having all the properties of typical fat but having fewer calories than typical fat. A non-caloric fat substitute, e.g. a sucrose polyester, likewise possesses all the typical fat characteristics, but is not absorbed after ingestion and thus is not metabolized. To be suitable for use as a pre-treatment ingredient in this invention, the fat must not demonstrate an activity that promotes reaction, decomposition of adverse interaction of cocoa polyphenols. Fats that are highly unsaturated are considered unsuitable for use as pre-treatment ingredients because these fats may generate free-radical species during processing. Accordingly, fats and fatty acids having relatively high levels of unsaturation, such as linoleic and linolenic acids, are considered unsuitable as polyphenol-conserving pre-treatment ingredients. Cocoa butter and fats obtained from genetically modified seed oils or modified seed oils having relatively low levels of unsaturation, e.g. high oleic sunflower oil or high oleic peanut oil would be especially preferred polyphenol-conserving pre-treatment ingredients.

Emulsifying agents, or emulsifiers, are also used as ingredients in the food products of the present invention. Emulsifying agents are well known to play a critical role in suspension rheology and are used throughout food manufacturing, especially confectionary and chocolate manufacturing, to enhance the rheology (i.e., reduce viscosity and/or yield value) of solids suspensions. Soy lecithin is one of the oldest and most widely used emulsifying agent. In chocolate, lecithin demonstrates a significant viscosity lowering effect when used at an optimum concentration of about 0.3% to about 0.7% by weight of the finished chocolate. Exemplary emulsifying agents useful in the present invention may be any of those emulsifying agents typically used in the art and include lecithin derived from vegetable sources such as soybean, safflower, corn, etc., fractionated lecithins, mono- and di-glycerides, di-acetyl tertaric acid esters of mono- and di-gycerides (also referred to as DATEM), monosodium phosphate derivatives of mono- and di-glycerides of edible fats or oils, sorbitan monostearate, polyoxyethylene sorbitan monostearate, hydroxylated lecithin, lactylated fatty acid esters of glycerol and propylene glycol, polyglycerol esters of fatty acids, propylene glycol mono- and di-esters of fats and fatty acids, and especially any emulsifying agents that may become approved for the U.S. Food and Drug Administration-defined soft candy category. It is considered within the skill of one in the art to select an emulsifying agent for use in the preparation of a food product of the present invention. In addition, other emulsifying agents that may be used include polyglycerol polyricinoleate (PGPR), ammonium salts of phosphatidic acid (e.g., YN), sucrose esters, oat extract, etc., and any emulsifying agent or combination, thereof, found to be suitable in chocolate or similar fat/solid system.

Selected combinations of emulsifying agents have been identified to provide the confectioneries of the present invention, particularly reduced-fat confectioneries, having improved rheology over confectioneries prepared using conventional emulsifying agents. Emulsifying agent combinations that are particularly useful in the present invention are combinations of lecithin, sucrose polyerucate (ER-290, sold by Mitsubishi Kasei Corporation, Japan; sucrose polystearate (sold by Mitsubishi Kasei Corporation, Japan), ammonium phosphatide, phosphated mono-di-glycerides/diacetyl tartaric acid of mono-glycerides (PMD/DATEM), or fractionated lecithin, with sucrose polyerucate and/or polyglycerol polyricinoleate (PGPR ADMUL Wol, sold by Quest International, Hoffman Estates, Ill.).

Advantageously, the emulsifying agent combinations of polyglycerol polyricinoleate, sucrose polyerucate, and soy lecithin, offer significant improvement in the rheology of the chocolates of the present invention. Use of these preferred emulsifying agent combinations provides the chocolates of this invention having enhanced viscosity and yield value.

When a reduced fat chocolate is prepared, a combination of emulsifying agents is used, i.e., a base emulsifying agent and a second emulsifying agent. The base emulsifying agent is added in an amount of less than 1.0% by weight, as limited by current U.S. Food and Drug Agency Standards of Identity. The amount of the base emulsifying agent present in the reduced-fat chocolates is about 0.1% to about 0.9%, preferably about 0.2% to about 0.8%, and more preferably about 0.4% to about 0.6% by weight, based on the total weight of the chocolate. Optionally, the mixture of the fat and solid-containing chocolate ingredients may be conched prior to addition of the base emulsifying agent.

Sucrose polyerucate may be used as either the base emulsifying agent and/or as the second emulsifying agent. When used as the second emulsifying agent, the sucrose polyerucate is present in an amount of about 0.4% to about 0.6% by weight, based on the total weight of the reduced fat chocolate. Sucrose polyerucate is particularly useful because it reduces both the plastic viscosity and yield value even when used at concentration greater than 1.0% by weight. Sucrose polyerucate may be present in an amount of less than about 1.0%, e.g. about 0.1% to about 0.9%, preferably about 0.2% to about 0.6%, and more preferably about 0.4%, to about 0.5% by weight, based on the total weight of the reduced fat chocolate.

Polyglycerol polyricinoleate (PGPR-Admul WOL from Quest Int'l.) is useful as the second emulsifying agent. Polyglycerol polyricinoleate, which is the partial polyglyceryl ester of inter-esterified castor oil fatty acids, has proven very useful in modifying the yield value of high-viscosity chocolates. The PGPR may be present in amount of about 0.05% to about 0.5%, preferably about 0.2% to about 0.35%, based on the total weight of the low fat chocolate.

The use of very small amounts of PGPR provides significant benefits. The combination of PGPR (0.5% by weight) with lecithin (0.5% by weight) reduces the yield value to zero. When the second emulsifying agent is polyglycerol polyricinoleate, it is present in an amount of about 0.2% to about 0.35% by weight, based on the total weight of the reduced fat chocolate.

When there is 20% total fat, the PGPR concentration can be as low as 0.05% by weight. When the reduced fat chocolate contains less than 23% by weight total fat, the PGPR, in combination with a base emulsifying agent, may be about 0.05% to about 0.5% by weight. Preferably, PGPR in combination with a base emulsifying agent may be present in an amount of about 0.2% to about 0.35% by weight, based on the total weight of the reduced fat chocolate.

The rheology of reduced-fat chocolates may be further improved by the use of a three component emulsifier combination. The addition of sucrose polyerucate (0.2% by weight) and PGPR (0.2% by weight) reduced the yield value over 70% of reduced fat chocolate containing 0.6% by weight lecithin and reduced the plastic viscosity over 45%, compared to the lecithin containing reduced fat chocolate.

The preferred emulsifying agent combinations include the combinations of lecithin-sucrose polyerucate, lecithin-polyglycerol polyricinoleate, sucrose polyerucate-polyglycerol polyricinoleate, and lecithin-sucrose polyerucate-polyglycerol polyricinoleate. Use of these preferred emulsifying agent combinations provides reduced-fat chocolates having a total fat content below 23% by weight, viscosity values of less than 100 poise, and yield values of less than 150 dynes/cm$^2$.

As used herein, the term "antioxidant compound" refers to compounds that prevent oxidation and function as a reducing agent or as an electron donor/receptor. According to their mode of action, antioxidants may be classified as free radical terminators, metal ion chelators, or as oxygen scavengers that react with oxygen. Suitable antioxidant compound classes include tannin, including condensed tannins and hydrolyzable tannins, quinones polyhydroxy compounds, phospholipids, tocol compounds or derivatives thereof. Exemplary antioxidants include, but are not limited to. The antioxidants also include reducing agents including such diverse materials as organic acids, such as ascorbic acid, stannous chloride, and tocopherols (vitamin E). Sulfur dioxide, preservative, can also function as an antioxidant. Di-lauryl thiodipropionate and thiodipropionic acid can function as preventive antioxidants by reacting with hydroparoxides.

As used herein, the term "flavoring agent" refers to flavored compounds or compositions used in food products and confectionary, particularly in chocolates, to impart a desired taste and aroma. A flavoring agent that is suitable for use as a pre-treatment ingredient is a flavor compound or composition that demonstrates an activity that prevents reaction, complexation, decomposition or adverse interaction of cocoa polyphenols with any of the other ingredients used in the preparation of these products or with any polyphenol-reactive material generated from or by the other ingredients during the preparation of these produces. Exemplary flavoring agents suitable for use as pre-treatment ingredients include vanillin, spices, and naturally expressed citrus or spice oils, which contain flavanoids and phenol-based flavorants, e.g. eugenol, which may function as a free radical terminator and may thus prevent reaction of cocoa polyphenols with any free radical species generated during production.

Chocolate used in foods in the United States is subject to a standard of identity established by the U.S. food and Drug Administration under the Federal Food, Drug and Cosmetic Act that sets out the requisite ingredients, and proportions thereof, of a confection to permit labelling of the confection as a "chocolate." The most popular chocolate or chocolate candy consumed in the United States is in the form of sweet chocolate or milk chocolate. Chocolate is essentially a mixture of solid-containing ingredients, including cocoa solids, suspended in fat. Milk chocolate is a confection which contains milk solids, milk tat, chocolate liquor, a nutritive carbohydrate sweetener, cocoa butter and may include a variety of other ingredients such as emulsifying agents, flavorings and other additives. Crumb chocolate is a type of milk chocolate, containing the same ingredients, however, wet milk and carbohydrate sweetener ingredients are pre-combined then co-dried, at elevated temperatures, to form a milk crumb that is then used to prepare the milk chocolate. Sweet chocolate contains higher amounts of chocolate liquor, but lower amounts of milk solids than milk chocolate. Semisweet chocolate requires at least 35% by weight chocolate liquor and is otherwise similar in definition to sweet chocolate. Dark chocolate, generally containing only chocolate liquor, a nutritive carbohydrate sweetener and cocoa butter, is by definition either a sweet chocolate or a semisweet chocolate. Buttermilk chocolate and skim milk chocolate differ from milk chocolate in that the milk fat comes from various forms of sweet cream buttermilk and skim milk, respectively. Skim milk requires the total amount of milk fat to be limited to less than the minimum for milk chocolate. Mixed dairy product chocolates differ from milk chocolate in that the milk solid includes any or all of the milk solids listed for milk chocolate, buttermilk chocolate or skim milk chocolate. White chocolate differs from milk chocolate in that it contains no non-fat cocoa solids. Non-standardized chocolates and those chocolates which have compositions which fall outside the specified ranges of the standardized chocolates. Chocolates are classified as "non-standardized" chocolates when a specified ingredient is replaced, either partially or completely, such as when the ingredient cocoa butter is replaced with vegetable oils or fats. Any additions or deleting to a chocolate recipe made outside the US FDA standards of identity for chocolate will prohibit use of the term "chocolate" to describe the confectionary. However, as used herein, the term "chocolate" refers to any standard of identity or non-standard of identity chocolate.

The reduced fat chocolates comprise a fat, solid-containing chocolate ingredients, and a combination of a base emulsifying agent and at least one other emulsifying agent. The chocolates are prepared by mixing the fat and chocolate ingredients, adding the base emulsifying agent to the mixture; and then adding at least one other emulsifying agent. When the emulsifying agent combination comprises more than two emulsifying agents, the third emulsifying agent is typically added after the second emulsifying agent. Any emulsifying agents added after the base emulsifying agent may be added in any order. The use of combinations of the emulsifying agents aids in dispersing the fat. The resulting confectioneries have the texture of a full-fat confectionery. The reduced fat chocolates are suitable for use in enrobing, extruding, or moulding operations. The chocolates have yield values of less than 250 dynes/cm$^2$, preferably less than 180 dynes/cm$^2$, more preferably less than 140 dynes/cm$^2$, and viscosities of less than 150 poise, preferably less than 100 poise, more preferably less than 75 poise.

Chocolate may take the form of solid pieces of chocolate, such as bars or novelty shapes, and may also be incorporated as an ingredient of other, more complex confections where chocolate is combined with and generally coats other foods such as caramel, peanut butter, nougat, fruit pieces, nuts, wafers, ice cream or the like. These foods are characterized as microbiologically shelf-stable of 65°–85° F. (18–20° C.) under normal atmospheric conditions.

The term "carbohydrate" refers to nutritive carbohydrate sweeteners, with varying degrees of sweetness intensity that are useful in the present invention, may be any of those typically used in the art and include, but are not limited to, sucrose, (e.g., from cane or beet), dextrose, fructose, lactose, maltose, glucose syrup solids, corn syrup solids, invert sugar, hydrolyzed lactose, honey, maple sugar, brown sugar, molasses and the like.

The food products of the present invention may additionally contain other ingredients such as milk solids, cocoa solids (cocoa powder), sugar substitutes, natural and artificial flavors (e.g., spices, coffee, salt, brown nut-meats, etc., as well as mixtures of these), proteins, and the like.

Sugar substitutes may be used to partially replace the nutritive carbohydrate sweetener, particularly in the production of reduced-calorie confectioneries and chocolates. As used herein, the term "sugar substitute" includes high potency sweeteners, sugar alcohols (polyols) and bulking agents, or combinations thereof. The high potency sweeteners include aspartame, cyclamates, saccharin, acesulfame, no-nesparidin dihydrochalcons, sucralose, alitame, stevia sweeteners, glycyrrhizin, thaumatin, and the like, and mixtures thereof. The preferred high potency sweeteners include aspartame, cyclamates, saccharin, and acesulfame-K. Examples of sugar alcohols may be any of those typically used in the art and include sorbitol, mannitol, xylitol, malticol, isomalt, lactitol and the like. The food products of the present invention may also contain bulking agents, typically used in combination with high potency sweeteners. The term "bulking agents" as defined herein may be any of those typically used in the art and include polydextrose, cellulose and its derivatives, maltodextrin, gum arabic, and the like.

The term "fermentation factor" is a numerical quantification of the level of fermentation of a batch of cocoa beans. Fermentation factors range from 100 (under/unfermented) to 400 (fully fermented). To assess the degree of fermentation, cocoa beans are typically subjected to a standard cut test for assessing quality as defined in industry grade standards. The bean halves are laid out on a board for visual inspection of color as well as detects which can arise during bean fermentation, drying and/or storage. Beans can be divided into four fermentation categories according to their color and appearance: (a) fully fermented, e.g., predominantly a brown hue; (b) partially fermented, e.g., purple/brown; (c) purple (under/fermented) ; and (d) slaty (very under-fermented and/or unferemented beans). Purple/brown beans include all beans showing any blue, purple or violet color on the exposed surfaces, whether suffused or as a patch. Purple beans should include all beans showing a completely blue, purple or violet color over the whole exposed surface. This should also include, irrespective of color, any beans which are slaty, but not predominantly so (wherein predominantly, in this context, means more than half).

The "fermentation factor" is determined using a grading system for characterizing the fermentation of the cocoa beans. Slaty, being under/unfermented, in designated as 1, purple as 2, purple/brown as 3 and brown as 4. The percentage of beans falling within each category is multiplied by the weighted number. Thus, the "fermentation factor" for a sample of 100% brown beans would be 100×4 or 400, whereas the fermentation factor for a sample of 100% purple beans would be 100×2 or 200. A sample or 50% slaty beans and 50% purple beans would have a fermentation factor of 150 [(50×1)+(50×2)]. Cut tests applicable to cocoa beans derived from the Trinitario and Forastero types may or may not be applicable to cocoa beans derived from the Criollo type, for example, where bean color variation ranging from fully purple to light tan can be encountered. Accordingly, the cut test based on color would not be applicable to specific cocoa genotypes lacking the anthocyanin pigments responsible for the purple color, such as the Catango (or Catongo) type whose beans are light tan in color. Other exceptions include "cocoa beans" derived from other Theobroma species, the Herrania species and their inter- and intra-specific crosses. The beans from these species are "tan" in color. For these types of beans the level of fermentation may be determined using a modified standard cut test. Using the modified test, the surface of the bean (halved) is inspected for the degree of lines, fissures or cracks which form during fermentation, rather than the change of color.

Figure 1A:
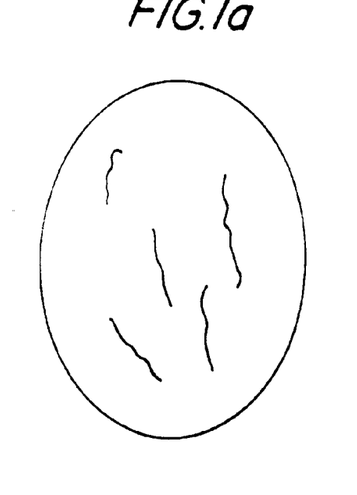
Figure 1B:
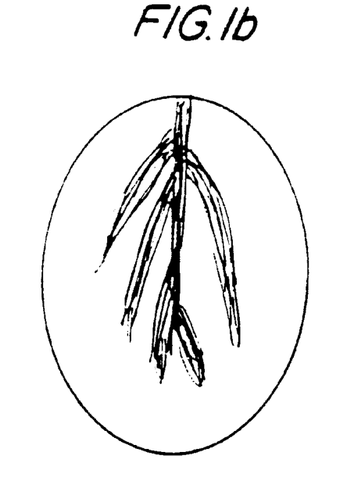
Figure 1C:
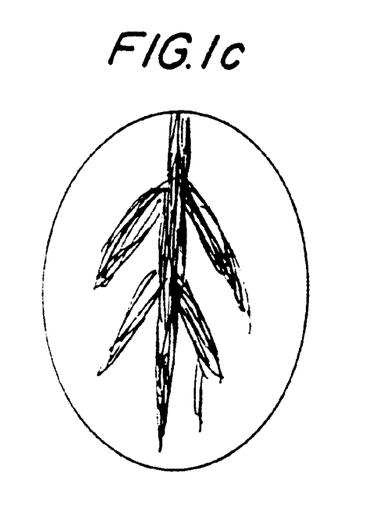
Figure 1D:
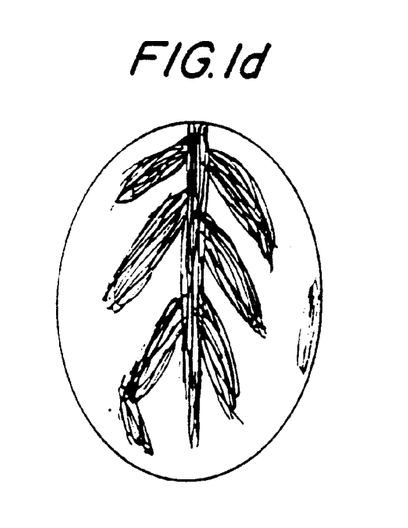

FIGS. 1(a)–(d) illustrate the change in the surface of the cut bean half during the fermentation of the cocoa bean. As can be seen from FIGS. 1(a)–(d), the number of lines/fissures and the extent to which they extend across the entire surface of the cut bean half increases as the bean is fermented. FIG. 1(a) depicts the cut bean half of an unfermented cocoa bean where the surface is relatively smooth. FIGS. 1(b)–(d) depict the cocoa beans as it is fermented, with FIG. 1 (d) illustrating the fully fermented cocoa bean. As the cocoa bean is fermented, the surface develops small branch-like lines or fissures. This modified test can also be used to approximate the fermentation factor wherein a cocoa bean corresponding to FIG. 1(a) is designated as 100, FIG. 1(b) as 200, FIG. 1(c) as 300 and FIG. 1(d) as 400. While the definitions of the aforementioned categories are a general guide, the assessment according to these categories is well within the skill of the ordinary skilled artisan well versed in chocolate and cocoa processing (see Wood et al., *Cocoa,* 4th Ed. (1985), incorporated herein by reference, especially pages 511 to 513). The numerical index, 1–4 or 100–400, and qualitative terms that are used herein to reflect the relative fermentation of cocoa beans and therefore related to the relative concentration of cocoa polyphenols in cocoa beans. A value of 1 or 100 would reflect unfermented beans possessing the highest relative concentration of cocoa polyphenols, that is, the total amount or nearly the total amount of cocoa polyphenols produced by the cocoa plant in the cocoa bean. A value of 4 or 400 would reflect fully fermented beans possessing the relative lowest concentration of cocoa polyphenols, that is, the remaining amount of cocoa polyphenols that did not react, decompose, or otherwise transform under fermentation, roasting, alkalization or other processing procedures. The actual cocoa polyphenol concentration of any cocoa bean sample or cocoa ingredient may be determined using the high performance liquid chromatographic (HPLC) technique described in Romanczyk, et al., U.S. Pat. No. 5,554,645.

The term "significant amount" means an amount which maintains the basic characteristics of the specified ingredients or composition or product.

The term "air average quality cocoa beans" refers to cocoa beans that have been separated from the pulp material and dried and are relatively free of mold and infestation. Such beans are a commercial commodity and form the feedstock for the next step in the production processes, e.g., infra-red heating, roasting, pressing, etc. The term includes any such bean that has been genetically modified or produced.

The term "raw freshly harvested cocoa beans" refers to seeds or beans freshly harvested from the cocoa pod and which have not been subjected to processing other than separation from the pulp. The term includes any such bean that has been genetically modified or produced.

A preferred embodiment of this invention is a process for providing a confectionery product having a conserved cocoa polyphenol concentration, comprising:

(a) mixing a carbohydrate ingredient with at least one pre-treatment ingredient to form a confectionery mix.

(b) combining the confectionery mix with at least one ingredient containing cocoa polyphenol, and (c) forming the polyphenol-containing confectionery product, wherein the product contains at least about 10% by weight more polyphenol than a product prepared without using the pre-treatment process according to step (a).

Another embodiment of this invention is a process of preparing a chocolate product having a conserved concentration of cocoa polyphenol; the process comprises:

(a) mixing at least one ingredient selected from the group consisting of milk ingredients and carbohydrate ingredients, with at least one pre-treatment ingredient to form a confectionery mix, (b) combining the confectionery mix with at least one ingredient containing cocoa polyphenol, (c) conching the combined ingredients, and (d) forming the polyphenol-containing chocolate product, wherein the product contains at least about 10% by weight more polyphenol than a product prepared without using the pre-treatment process according to step (a).

In another embodiment of this invention, confectionery products, particularly chocolate products, having a conserved concentration of cocoa polyphenol, and particularly, cocoa polyphenol oligomers 5–12 may be prepared using a split milling, or split refining process comprising:

(a) mixing at least one ingredient selected from the group consisting of milk ingredients and carbohydrate ingredients, with at least one pre-treatment ingredient to form a confectionery mix, (b) milling or refining the confectionery mix, (c) combining the milled confectionery mix with at least one ingredient containing cocoa polyphenol and having a particle size equal to or less than that desired in the confectionery product or chocolate product, (d) conching the combined ingredients, and (e) forming the polyphenol-containing confectionery or chocolate product, wherein the product contains at least about 10% by weight more polyphenol than a product prepared without using the pre-treatment process according to step (a).

In yet another embodiment, chocolates having a strong chocolate flavor and conserved concentrations of cocoa polyphenols, and particularly, cocoa polyphenol oligomers 5–12 may be prepared using a split conching process comprising:

(a) mixing at least one ingredient selected from the group consisting of milk ingredients and carbohydrate ingredients, with at least one pre-treatment ingredient to form a confectionery mix, (b) conching the confectionery mix, (c) combining at least one ingredient containing cocoa polyphenol with the conched confectionery mix, (d) refining, then conching, the resulting mixture, and (e) forming the polyphenol-containing chocolate product, wherein the product contains at least about 10% by weight more polyphenol than a product prepared without using the pre-treatment process according to step (a).

Another embodiment of the split conching process, providing chocolates having a strong chocolate flavor and conserved concentrations of cocoa polyphenols, particularly, cocoa polyphenol oligomers 5–12, comprises:

(a) mixing at least one ingredient selected from the group consisting of milk ingredients and carbohydrate ingredients, with at least one pre-treatment ingredient to form a confectionery mix, (b) conching the confectionery mix at a temperature of about 60° C. to about 90° C., (c) cooling the conched confectionery mix to a temperature of about 35° C. to about 50° C., (d) combining at least one ingredient containing cocoa polyphenol with the cooled, conched confectionery mix, (e) refining, then conching, the resulting mixture, and (f) forming the polyphenol-containing chocolate product, wherein the product contains at least about 10% by weight more polyphenol than a product prepared without using the pre-treatment process according to step (a).

Preferably the polyphenol-containing food products prepared by the processes of this invention contain about 15% by weight more cocoa polyphenol than a polyphenol-containing food product prepared without using the pre-treatment process according to step (a); more preferably, the food product of this invention contains about 20% by weight more cocoa polyphenol than a food product prepared without using step (a). The comparative polyphenol-conservation value of 10%, 15% and 20% refer to the difference between the conserved concentration of polyphenol in a test sample and the conserved concentration of the polyphenol in a control sample. The conserved concentration of polyphenol in a sample, expressed as percentage, is the concentration of polyphenol in the sample, relative to the concentration of polyphenol in a theoretical sample having 100% conservation. The increased concentration of cocoa polyphenol retained, or conserved, in the food products of this invention may be measured by analysis of a single oligomer, such as cocoa polyphenol pentamer, as an indicator of improvement in retention. Significantly, the use of the polyphenol pentamer as the analytical standard also provides an indication of the concentration of the process-sensitive polyphenol oligomers 5–12 retained, or conserved, in the food products of this invention.

The food products of this invention contain at least a carbohydrate-containing ingredient or a protein-containing ingredient, or a mixture thereof. According to the processes of this invention, at least one of these ingredients is mixed first with at least one pre-treatment ingredient. Preferably, if both a carbohydrate-containing ingredient and a protein-containing ingredient are present in the food product, both ingredients are mixed with at least one pre-treatment ingredient prior to mixing with the polyphenol-containing ingredient. Optionally, the carbohydrate-containing ingredient, protein-containing ingredient, or mixture thereof, may be milled or refined prior to mixing with at least one pre-treatment ingredient. Alternatively, the mixture of carbohydrate and/or protein-containing ingredients with the pre-treatment ingredient(s) may be milled or refined after mixing.

Optionally, the protein-containing ingredient may be a milk ingredient. According to the process of the present invention, the process of preparing a milk chocolate, having a conserved concentration of cocoa polyphenol, comprises mixing both milk ingredients and carbohydrate ingredients with at least one pre-treatment ingredient. Milk ingredients, as used herein, include any milk-based ingredient commonly used in food manufacturing, and particularly, confectionery or chocolate manufacturing. Exemplary milk ingredients include liquid milk, milk proteins (casein, whey protein), condensed mil, sweetened condensed milk, evaporated milk, milk crumb, milk powder, re-constituted milk, malted milk, malted milk powder, cultured milk powders, and the like.

Preferably, in each of the above-described processes of this invention, the pre-treatment ingredient is selected from the group consisting of fat, an emulsifying agent, a cocoa ingredient, an antioxidant compound, a flavoring agent and mixtures thereof. The pre-treatment fat ingredient may be selected from any fat described hereinabove, but is preferably cocoa butter. The pre-treatment emulsifying agent ingredient may be selected from any emulsifying agent described hereinabove, but is preferably lecithin, fractionated lecithin, or mixtures thereof. The pre-treatment cocoa ingredient may be any cocoa ingredient described hereinabove, but is preferably obtained from cocoa beans having a fermentation factor of 300 or greater. The pre-treatment antioxidant and flavoring agent ingredients may be any of the above-described antioxidant and flavoring agent ingredients.

Preferably, in each of the above-described processes of this invention, the pre-treatment ingredient is a mixture of fat and an at least one emulsifying agent. More preferably, the pre-treatment ingredient is a mixture of lecithin and cocoa butter.

In each of the above-described processes of this invention, the polyphenol-containing ingredient may be selected from the group consisting of a cocoa ingredient comprising procyanidins, an extract of cocoa beans or a cocoa ingredient comprising procyanidins, synthesized derivatives of the extracts of cocoa beans or a cocoa ingredient comprising procyanidins, synthesized cocoa polyphenol compounds, and synthesized derivatives of synthesized cocoa polyphenol compounds. The polyphenol-containing cocoa ingredient is preferably a cocoa solids-containing material derived from shell-free cocoa nib and includes chocolate liquor and partially or fully defatted cocoa solids (e.g., cake or powder), and the like. Advantageously, the polyphenol-containing cocoa ingredient is obtained from cocoa beans having a fermentation factor less than 300; preferably, the cocoa ingredient is obtained from cocoa beans have a fermentation factor less than 275, more preferably, from cocoa beans have a fermentation factor less than 250; more preferably, from cocoa beans have a fermentation factor less than 225, even more preferably, from cocoa beans have a fermentation factor less than 200, more preferably, from cocoa beans have a fermentation factor less than 150, and most preferably, from cocoa beans have a fermentation factor less than 125.

A preferred embodiment of this invention is a process for providing a dark chocolate having a conserved cocoa polyphenol concentration, comprising:
  (a) mixing a carbohydrate nutritive sweetener with lecithin and cocoa butter to form a confectionery mix,
  (b) combining the confectionery mix with a chocolate liquor obtained from cocoa beans having a fermentation factor less than 300, and
  (c) forming the polyphenol-containing dark chocolate, wherein the chocolate contains at least about 10% by weight more polyphenol than a dark chocolate prepared without using the pre-treatment process according to step (a).

A preferred embodiment of this invention is a process for providing a milk chocolate having a conserved cocoa polyphenol concentration, comprising:
  (a) mixing a milled or refined carbohydrate nutritive sweetener and a milled or refined milk powder with lecithin and cocoa butter to form a confectionery mix,
  (b) combining the confectionery mix with a chocolate liquor obtained from cocoa beans having a fermentation factor less than 300, and
  (c) forming the polyphenol-containing milk chocolate, wherein the chocolate contains at least about 10% by weight more polyphenol than a milk chocolate prepared without using the pre-treatment process according to step (a).

In a preferred embodiment, at least two cocoa ingredients having varying concentrations of cocoa polyphenols are used to prepare the food products and confectionery products of this invention. For example, a first cocoa ingredient, derived from fermented cocoa beans having a fermentation factor of 300 or greater (having a low cocoa polyphenols concentration, but a high chocolate flavor/aroma content) may be used either as the pre-treatment ingredient, or in combination with other pre-treatment ingredients. A second cocoa ingredient, derived form under-fermented beans having a fermentation factor less than 300 (having a higher cocoa polyphenols concentration, but a lower chocolate flavor/aroma content) may be used as the polyphenol-containing cocoa ingredient. The use of such a cocoa-ingredient blend allows for the production of a chocolate having strong flavor/aroma characteristics as well as enhanced concentrations of cocoa polyphenols.

In another embodiment of this invention, the ingredient containing cocoa polyphenol may be a combination of chocolate liquor and cocoa powder, wherein the liquor and powder are obtained from cocoa beans having a fermentation factor less than 300. Preferably, the chocolate liquor and cocoa powder are obtained from cocoa beans having a fermentation factor less than 275, more preferably, from cocoa beans having a fermentation factor less than 250, more preferably, from cocoa beans having a fermentation factor less than 225, even more preferably, from cocoa beans having a fermentation factor less than 200, more preferably, from cocoa beans having a fermentation factor less than 150, and most preferably, from cocoa beans having a fermentation factor less than 125.

Additionally, each of the above-described processes may further comprise the step of adding a second emulsifying agent, which may be added either during or after conching. The second emulsifying agent may be selected from any of the above-described emulsifying agents. Preferably, the second emulsifying agent may be lecithin, sucrose polyerucate, ammonium phosphatide, polyglycerol polyricinoleate, phosphated mono- and di-glycerides/di-acetyl tartaric acid of mono-glycerides (PMD/DATEM), fractionated lecithin, or mixtures thereof.

Accordingly, a novel chocolate of the present invention, having a high cocoa polyphenol concentration, may be prepared according to any of the above-described process further comprising the step of combining the confectionery mix with a chocolate liquor and a cocoa powder. The novel chocolate may be prepared by the process comprising the steps of:
  (i) combining carbohydrate or carbohydrate and milk ingredients with a pre-treatment ingredient comprised of lecithin and optionally, at least one ingredient selected from the group consisting of a fat, a cocoa ingredient, an antioxidant compound and a flavoring agent,
  (ii) using a combination of a chocolate liquor and a cocoa powder as the polyphenol-containing ingredient, and
  (iii) adding a second emulsifying agent either during or after conching, and
  (iv) forming the polyphenol-containing chocolate, wherein the chocolate contains at least about 10% by weight more cocoa polyphenol than a polyphenol-containing chocolate prepared without using the pre-treatment process according to step (i).

Another embodiment of the invention relates to a food product, and a process of preparing the product, having enhanced concentrations of cocoa polyphenols derived from a cocoa polyphenol-containing ingredient. Preferred cocoa polyphenol-containing ingredients may be selected from the group consisting of extracts of cocoa beans or a cocoa ingredient comprising procyanidins, synthesized derivatives, synthesized cocoa polyphenol compounds, and synthesized derivatives of synthesized cocoa polyphenol compounds. The polyphenol ingredient may be mixed with other product ingredients during the processing, but is preferably mixed with other ingredients at or near the end of processing, or added to the product after processing (i.e., spraying onto the product).

Preferably the polyphenol-containing food products prepared by the processes of this invention contain about 15% by weight more cocoa polyphenol than a polyphenol-containing product prepared without using the pre-treatment process according to step (a); more preferably, the food products of this invention contain about 20% by weight more cocoa polyphenol than a food product prepared without using step (a). The percentage improvement of cocoa polyphenol concentration, as defined herein, may be measured using a single oligomer, such as pentamer, as an indicator of improvement in retention.

Novel food products containing cocoa polyphenols, particularly enhanced concentrations of cocoa polyphenols, may be prepared by any of the above-described processes. The novel products are distinguishable from conventional products either because (1) the inventive products contain elevated concentrations of cocoa polyphenols relative to comparative conventional products (i.e., chocolates, chocolate-flavored confections, etc.) and/or (2) the inventive products contain cocoa polyphenols in contrast to comparative products which do not contain cocoa polyphenols (i.e., rice cakes, edible foods without chocolate flavor/aroma, etc.).

One embodiment of this invention relates to a food product containing a cocoa polyphenol ingredient. Preferably, the product comprises at least 1 μg cocoa polyphenols per gram product, preferably at least 2 μg, more preferably at least 5 μg, and most preferably at least 10 μg cocoa polyphenols per gram product. According to one preferred embodiment, the product comprises at least 25 μg cocoa polyphenols per gram product, preferably at least 50 μg, more preferably at least 100 μg, and most preferably at least 150 μg cocoa polyphenols per gram product.

Another embodiment of the invention relates to a chocolate comprising at least 3,600 μg cocoa polyphenol per gram chocolate, preferably at least 4,000 μg, advantageously at least 4,500 μg, more preferably at least 5,000 μg, and most preferably at least 5,000 μg cocoa polyphenols per gram chocolate. According to one preferred embodiment, the chocolate contains at least 6,000 μg cocoa polyphenols per gram chocolate, preferably at least 6,500 μg, more preferably at least 7,000 μg, and most preferably at least 8,000 μg cocoa polyphenols per gram chocolate.

Another embodiment of the invention relates to a chocolate comprising at least 100 μg cocoa polyphenol pentamer per gram of chocolate, preferably the chocolate contains at least 150 μg, preferably the chocolate contains at least 200 μg, preferably the chocolate contains at least 250 μg, preferably the chocolate contains at least 300 μg, more preferably, at least 325 μg, and most preferably, at least 350 μg cocoa polyphenol pentamer per gram chocolate. According to one preferred embodiment, the chocolate contains at least 375 μg cocoa polyphenol pentamer per gram chocolate, preferably, at least 400 μg, more preferably at least 425 μg, and most preferably, at least 450 μg cocoa polyphenol pentamer per gram chocolate.

Yet another embodiment of the invention relates to a milk chocolate containing milk solids and comprising at least 1,000 μg cocoa polyphenols per gram chocolate, preferably at least 1,250 μg, more preferably at least 1,500 μg, and most preferably at least 2,000 μg cocoa polyphenols per gram chocolate. According to one preferred embodiment, the milk chocolate contains at least 2,500 μg cocoa polyphenols per gram chocolate, preferably at least 3,000 μg, more preferably at least 4,000 μg, and most preferably at least 5,000 μg cocoa polyphenols per gram chocolate.

Another embodiment of the invention relates to a milk chocolate containing milk solids and comprising at least 85 μg cocoa polyphenol pentamer per gram chocolate, preferably at least 90 μg, more preferably at least 100 μg, and most preferably at least 125 μg cocoa polyphenol pentamer per gram chocolate. According to one preferred embodiment, the milk chocolate contains at least 150 μg cocoa polyphenol pentamer per gram chocolate, preferably at least 175 μg, more preferably at least 200 μg, and most preferably at least 250 μg cocoa polyphenol pentamer per gram chocolate.

The Examples which follow are intended as an illustration of certain preferred embodiments of the invention, and no limitation of the invention is implied. In the following Examples 3–9, the "fat" may be cocoa butter or mixtures of cocoa butter and milk fat. The milk fat may be used in a concentration, as desired, to provide a finished chocolate having a preferred hardness and snap. In the following Examples 3–9, the "CP Liquor" and "CP Cocoa Powder" are cocoa polyphenol-containing chocolate liquor and cocoa polyphenol-containing cocoa powder, respectively, obtained from cocoa beans having a fermentation factor of less than 300.

EXAMPLE 1

Method of Obtaining Cocoa Polyphenol Cocoa Solids from Cocoa Beans

Commercially available cocoa beans having an initial moisture content of from about 7 to 8 percent by weight were pre-cleaned using an 11"×56" Scalperator (manufactured by Carter Day International, Minneapolis, Minn., USA). Approximately 600 bags of cocoa beans (39,000 kg) were pre-cleaned over a 6.5 hour time period. The beans were fed into the inlet hopper where the flow rate was regulated by a positive feed roll. The beans were fed onto the outside of a rotating wire mesh scalping reel. The beans passed through the wire mesh reel and subsequently through an air aspiration chamber where light dirt, dust and strings were aspirated out of the product stream. The beans that did not pass through the scalping reel were conveyed to the reject stream. This reject stream consisted of large clumps of beans, sticks, stones, etc. The amount of resultant reject was approximately 150 kg, or 0.38% of the starting material. The resulting pre-cleaned product weighed about 38,850 kg and was passed to the bean cleaning step.

The pre-cleaned bean products from the Scalperator were then further cleaned using a Camas International SV4-5 Air Fluidized Bed Density Separator (AFBDS, manufactured by Camas International, Pocotello, Id., USA). About 38,850 kg of cocoa bean products were fed into the AFBDS over a time period of about 6.5 hours. The apparatus removed substantially all heavy impurities such as stones, metal, glass, etc. from the beans, as well as lighter unusable material such as moldy and infested cocoa beans, resulting in a cleaned bean product which contained substantially only usable cocoa beans. The resulting heavy impurities removed weighed about 50 kg and the light unusable materials weighed about 151 kg. A total of about 38,649 kg of cleaned beans was obtained after both the pre-cleaning and cleaning steps described hereinabove (99.1% yield after cleaning).

The cleaned cocoa beans were then passed through a infra-red heating apparatus. The apparatus used was the Micro Red 20 electric infra-red vibratory Micronizer (manufactured by Micronizing Company (U.K.) Limited, U.K.). The Micronizer was run at a rate of about 1,701 kilograms per hour. The depth of beans in the vibrating bed of the Micronizer was about 2 inches or about 2–3 beans deep. The surface temperature of the Micronizer was set at about 165° C., thereby producing in internal bean temperature (IBT) of about 135° C. in a time ranging from 1 to 1.5 minutes. This treatment caused the shells to dry rapidly and separate from the cocoa nib. Since substantially all of the cocoa beans fed into the Micronizer were whole beans and were substantially free of small broken pieces of bean or shell, no sparks or fires were observed during the infra-red heating step. The broken pieces separated by the vibrating screen prior to the Micronizer were re-introduced into the product stream prior to the winnowing step.

The beans after the Micronizer had a moisture content of about 3.9% by weight. The beans emerged from the Micronizer at an IBT of about 135° C. and were immediately cooled to a temperature of about 90° C. in about three minutes to minimize additional moisture loss. The total beans available after the heating step was about 36,137 kg.

The beans were then subjected to winnowing using a Jupiter Mitra Seita winnower (manufactured by Jupiter Mitra Seita, Jakarta, Indonesia). The winnowing step cracked the beans to loosen the shells and separated the lighter shells from the nibs while at the same time minimizing the amount of nib lost with the shell reject stream. The feed rate into the winnower was about 1,591 kg per hour. The resultant products included about 31,861 kg of usable nibs and 4,276 kg of reject shells. The overall yield of usable nibs from starting material was about 81.7%.

The resulting cocoa nibs were pressed using a Dupps 10-6 Pressor (manufactured by The Dupps Company, Germantown, Ohio, USA). A steady, consistent feed of about 1,402 kg per hour of nibs was fed into two screw presses to extract butter. The press produced about 16,198 kg of cocoa butter which contained about 10% cocoa solids, and about 15,663 kg of cocoa solids which contained about 10% butter.

The cocoa butter was further processed using a Sharples P3000 decanting centrifuge (manufactured by Jenkins Centrifuge Rebuilders, N. Kansas City, Mo., USA). Centrifugation reduced the solids content in the butter to about 1–2% solids and provided about 13,606 kg of butter and 2,592 kg of cocoa solids containing about 40 to 45% butter. The butter containing 1–2% solids was further processed using a plate and frame filter (manufactured by Jupiter Mitra Seita) which removed the remaining solids from the butter and provided about 13,271 kg of clear cocoa butter and about 335 kg of cocoa solids containing 40–45% butter.

The cocoa solids removed from the centrifuge and the filter press contained about 40–45% fat and were pressed in a batch hydraulic press to produce 10% fat cocoa cake. This material produced about 1,186 kg of clear butter and 1,742 kg of cocoa solids.

The total clear butter yield from the incoming beans was 14,456 kg, or 37.1%. The total cocoa solids produced from the incoming beans was 17,405 kg, or 44.6%.

Analysis of the actual cocoa polyphenol content of the cocoa beans and cocoa-containing products produced therefrom, may be conducted using the high performance liquid chromatographic (HPLC) technique described in Romanczyk, et al., U.S. Pat. No. 5,554,645. A sample of cocoa powder, produced according to the above-described process from unfermented cocoa beans (fermentation factor 100), was analyzed according to the above-referenced method and shown to contain the following polyphenol concentrations: a total polyphenol concentration of 32,743 $\mu$g of polyphenol per gram of cocoa powder, a monomer concentration of 9,433 $\mu$g/g, a dimer concentration of 5,929 $\mu$g/g, trimer concentration of 5,356 $\mu$g/g, tetramer concentration of 4,027 $\mu$g/g, pentamer concentration of 3,168 $\mu$g/g, hexamer concentration of 2,131 $\mu$g/g, heptamer concentration of 1,304 $\mu$g/g, octamer concentration of 739 $\mu$g/g, nonamer concentration of 439 $\mu$g/g.

EXAMPLE 2

Production of Chocolate Liquor Containing Cocoa Polyphenols

Fair average quality (FAQ) cocoa beans having an initial moisture content 7.4% by weight and a fermentation factor level of 233 (31% slaty, 29% purple, 22% purple brown and 17% brown) were selected as the starting material. The cocoa beans were then passed through an infra-red heating apparatus. The apparatus used was an infra-red vibrating micronizer (manufactured by Micronizer Company (U.K.) Limited, U.K.). The feed rate of beans through the infra-red heater and the infra-red heater bed angle were varied to control the amount of heat treatment the beans received. The amount of time the beans spent in the infra-red heater (residence time) was determined by the bed angle and the feed rate. The times used to prepare the example material are listed in the Table 1 below. At the outlet of the micronizer the IBT of the beans was measured, these values are also shown in Table 1.

A 1 kg sample of infra-red heated beans, collected off the infra-red heater at different IBTs, were cracked into smaller pieces. This is done to facilitate the separation of the nib from the shell. The laboratory piece of equipment used to remove the shell was the Limiprimita Cocoa Breaker made by the John Gordon Co. LTD. of England. The cracked beans were next passed through a laboratory scale winnowing system, using a Catador CC-1 manufactured by the John Gordon Co. LTD, England.

The cocoa nibs were next milled into a coarse liquor using a Melange made by Pascall Engineering Co. LTD, England. This device crushes and grinds the nibs into a chocolate liquor. The normal operating temperature for the liquor in the Melange in approximately 50° C. This same process of taking nibs to a coarse liquor could be done on a larger production scale using other types of mills, such as a Carle & Montanari Mill. The cocoa nibs were ground in the Melange for one hour. The concentration of cocoa polyphenols was measured for the samples relative to the infra-red heated temperatures. These values are contained in the Table 1 below.

TABLE 1

| IBT ° C. | Residence Time in Micronizer, Seconds | % Moisture in Finished Liquor | $\mu$g/g Pentamer in Defatted Liquor | $\mu$g/g Of Total Polyphenols in Defatted Liquor |
|---|---|---|---|---|
| 107 | 42 | 3.9 | 3,098 | 39,690 |
| 126 | 82 | 1.87 | 1,487 | 28,815 |
| 148 | 156 | 1.15 | 695 | 23,937 |

EXAMPLE 3

Control Sample

A standard chocolate batch process using a 10 lb. Sigma blade mixer (manufactured by Teledyne Read Co., York, Pa.) was used to mix together the following ingredients.

| Ingredient | % Concentration (by weight) |
|---|---|
| Sucrose | 40% |
| Chocolate Liquor | 7% |
| CP Liquor | 49% |
| Fat | 3.5% |
| Lecithin | 0.5% |

The ingredients were added into a 10 lb. Sigma blade mixer (manufactured by Teledyne Read Co., York, Pa.), in order of chocolate liquor and CP liquor, sucrose, cocoa butter, and flavorings. The resulting batch of ingredients was mixed until homogeneous, at about 35° C. to about 90° C. The CP liquor, prepared according to Example 2, used to prepare the chocolate samples contained 1150 μg polyphenol pentamer per gram of CP liquor. The mixture was refined to a micrometer particle size of 20 microns, conched and standardized (adjustment of viscosity and/or fat content to obtain chocolate with desired properties). The samples were analyzed for cocoa polyphenol concentration using the high performance liquid chromatographic (HPLC) technique described in Romanczyk, et al., U.S. Pat. No. 5,554,645 after mixing or after standardization.

EXAMPLE 4

Test chocolates were prepared using the same recipe and ingredients as Examples 3. The lecithin and fat were combined and mixed, using a 10 lb. Sigma blade mixer until homogeneous. The resulting fat/lecithin mixture was added to the granulated sucrose in a second 10 lb. Sigma mixer. The sucrose, fat and lecithin were mixed at about 35° C. to about 90° C. until homogeneous. The remaining ingredients, including the chocolate liquor having a high cocoa polyphenol concentration, were added and mixed until homogeneous. The resulting mixture was refined to a micrometer particle size of about 20 microns, conched, standardized and analyzed for cocoa polyphenol concentrations as in Example 3.

Table 2 lists the comparative results from a set of chocolates prepared according to the processes described in Examples 3 (Control) and 4 (Test). The chocolate liquor, used to prepare these chocolates, contained 1150 μg polyphenol pentamer per gram of chocolate liquor. Assuming 100% conservation of polyphenol concentration, the chocolates would contain 570 μg of polyphenol pentamer per gram of chocolate. Pentamer concentration of the Test samples was determined directly after initial batch mixing.

TABLE 2

| Sample | Pentamer (μg) | | % Increased Conservation |
|---|---|---|---|
| Control-1 | 361 | | |
| Test-1 | 418 | 73.3% | 10% |
| Control-2 | 360 | | |
| Test-2 | 472 | 82.8 | 19.6% |
| Control-3 | 313 | | |
| Test-3 | 385 | 67.5 | 12.6% |

Each test sample showed at least about a 10% by weight increase in polyphenol concentration over the control sample.

EXAMPLE 5

A control and test chocolate were prepared using the same ingredients and in a manner substantially similar to Examples 3 and 4, except that the concentration of lecithin was increased to 0.75% by weight. Pentamer concentration of these chocolates was measured after standardization (finished chocolate). The chocolate sample prepared according to the above test process contained 545.5 μg pentamer per gram of chocolate (95.7% conservation of pentamer), whereas the chocolate prepared according to the control process contained 439.6 μg pentamer per gram of chocolate (77.1% conservation of pentamer). Accordingly, the test chocolate, prepared by the inventive process, retained 18.6% by weight more cocoa polyphenol pentamer than the control chocolate.

EXAMPLE 6

A control and test dark chocolate were prepared according to the processes described in Examples 3 and 4, using the ingredients within the concentration ranges set forth below. The selection of the appropriate ingredients and ingredient amounts within the given range to prepare a chocolate is readily performed by one skilled in the art, without undue experimentation.

| Ingredient | % Concentration Range (by weight) |
|---|---|
| Sucrose | 35–55% |
| CP Liquor | 30–65% |
| Fat | 1–35% |
| Lecithin | 0.25% |

The chocolate liquor used to prepare the chocolates in these Examples contained 7819 μg total procyanidins per gram of chocolate liquor and 1300 μg pentamer per gram of chocolate liquor. The total procyanidin content represents the total cocoa polyphenol content of the liquor. Assuming 100% conservation of polyphenol concentration, the chocolates would contain 615 μg polyphenol pentamer per gram of chocolate. The test dark chocolate, prepared according to the process of Example 4, contained 502 μg pentamer (81.6% conservation) and 7091 μg total procyanidin (90.6% conservation) per gram of chocolate. The control dark chocolate, prepared according to the process of Example 3, contained 421 μg pentamer (68.5% conservation) and 6292 μg total procyanidin (80.5% conservation) per gram of chocolate. Accordingly, the test chocolate sample prepared using the inventive process retained 13.1% by weight more cocoa polyphenol pentamer and 10.2% by weight more total procyanidins than the control chocolate sample.

EXAMPLE 7

Dark chocolates were prepared according to the process described below, using the following general recipe:

| Ingredient | % Concentration Range (by weight) |
|---|---|
| Sucrose | 35–55% |
| Chocolate Liquor | 15–30% |
| CP Liquor | 10–20% |
| Fat | 0–15% |
| Lecithin | 0.1–1.0% |

The lecithin and fat were combined and mixed in a Buhler Paste Mixer (sold by Buhler Refiner Co., Minneapolis, Minn.) until homogeneous. The resulting fat/lecithin mixture was added to the sucrose in Petzholdt conches, models PVW 2000 and PVW 3000 (manufactured by J.S. Petzholdt Inh. H. Pilz., Frankfurt, Germany) and mixed at about 35° C. to about 90° C. until homogeneous. The remaining ingredients, including the chocolate liquor and the CP liquor were added to the lecithin/fat/sucrose mixture and mixed until homogeneous. The resulting mixture was refined to a micrometer particle size of about 20 microns, conched, standardized and analyzed for cocoa polyphenol concentration as in Example 3.

The combined chocolate liquors used in this Example could provide a dark chocolate containing a total procyanidin concentration of 2933 μg and a pentamer concentration of 162 μg per gram of chocolate. Two samples of the dark chocolate were prepared according to the above process and were determined to contain 158 μg pentamer and 2845 μg total procyanidins and 140 μg pentamer and 2866 μg total procyanidins, respectively.

EXAMPLE 8

A dark chocolate was prepared according to the process described below, using the following general recipe:

| Ingredient | % Concentration Range (by weight) |
| --- | --- |
| Sucrose | 15–35% |
| CP Liquor | 40–75% |
| CP Cocoa Powder | 1–10% |
| Fat | 1–10% |
| Vanillin | 0.01–0.05% |
| Lecithin | 0.1–1.0% |

Using a 10 lb. Sigma blade mixer, the lecithin and fat were combined and mixed until homogeneous. The resulting fat mixture was added to the granulated sucrose in a second 10 lb. Sigma mixer. The sucrose, fat and lecithin were mixed at about 35° C. to about 90° C. until homogeneous. The remaining ingredients, including the CP liquor and CP cocoa powder, were added and mixed until homogeneous. The resulting mixture was refined to a micrometer particle size of about 20 microns, conched, standardized and analyzed for cocoa polyphenol concentration as in Example 3. The chocolate liquor used to prepare the chocolates in this Example contained a total of 1000 μg pentamer per gram of chocolate liquor and the cocoa powder contained 1700 μg pentamer per gram of powder. Assuming 100% conservation of polyphenol concentration, the chocolates prepared according to the recipe above would contain of 768 μg polyphenol pentamer per gram of chocolate. This dark chocolate contained 732 μg pentamer per gram of chocolate, and thus retained over 95%, by weight, of the desired polyphenol pentamer present in the polyphenol pentamer-containing ingredients used to prepare the chocolate.

EXAMPLE 9

A milk chocolate was prepared according to the process described below, using the following general recipe:

| Ingredient | % Concentration Range (by weight) |
| --- | --- |
| Sucrose | 35–55% |
| Milk Ingredient | 12–25% |
| CP Liquor | 10–20% |
| Fat | 15–25% |
| Emulsifier | 0.1–1.0% |

At least 21% of the fat and at least 30% of the emulsifier were combined and mixed until homogeneous, and the resulting fat mixture was added to the sucrose and milk ingredients, and mixed. The CP liquor was added to that mixture, and mixed until homogeneous. The resulting mixture was refined, conched, standardized by addition of the remaining fat and emulsifier, and analyzed for cocoa polyphenol concentration as in Example 3. Assuming 100% conservation of polyphenol concentration, the chocolate liquor used to prepare this chocolate, would provide a milk chocolate containing 120 μg pentamer per gram of chocolate. The milk chocolate, prepared according to the above process, contained 115 μg pentamer per gram of chocolate, and thus retained over 95%, by weight, of the desired polyphenol pentamer present in the polyphenol pentamer-containing ingredient used to prepare the chocolate.

Other variations and modifications, which will be obvious to those skilled in the art, are within the scope and teachings of this invention. This invention is not to be limited except as set forth in the following claims.

We claim:

1. An improved food product containing cocoa polyphenols, the improvement being the conservation of the cocoa polyphenols during the processing of one or more cocoa-containing ingredients, which contain cocoa polyphenols, into the improved food product.

2. The food product of claim 1, wherein the food polyphenol is a cocoa procyanidin, and wherein the food ingredients include a carbohydrate ingredient and/or a milk ingredient which is pretreated with an antioxidant, an emulsifier, a fat, a flavorant, or mixtures thereof prior to the addition of the cocoa ingredient.

3. The food product of claim 2, wherein the pretreatment is with the emulsifier, the fat, or mixtures thereof.

4. The food product of claim 3, wherein the emulsifier is lecithin and the fat is cocoa butter.

5. The food product of claim 1, where the cocoa ingredient is selected from the group consisting of chocolate liquor, partially defatted or fully defatted cocoa solids, cocoa extract, synthetic cocoa procyanidin or derivative thereof, and mixtures thereof.

6. The food product of claim 5, wherein the cocoa ingredient is the chocolate liquor or a mixture of the chocolate liquor with the cocoa solids.

7. The food product of claim 2, wherein at least one of the cocoa ingredients is prepared from cocoa beans having a fermentation factor of less than 300.

8. The food product of claim 2, wherein the food product is a chocolate.

9. The food product of claim 8, wherein the chocolate is a dark chocolate.

10. A food product comprising (a) one or more cocoa ingredients which contain cocoa polyphenols in combination with (b) a carbohydrate ingredient and/or (c) a milk ingredient which are pretreated with an antioxidant, an emulsifier, a fat, a flavorant, or a mixture thereof before the addition of the cocoa ingredient(s).

11. The food product of claim 10, which contains at least about 10% by weight more cocoa polyphenols, measured as total cocoa procyanidins, than a food product prepared with a carbohydrate ingredient and/or a milk ingredient that is not pretreated.

12. The food product of claim 11, wherein the food product contains about 15% by weight more cocoa polyphenols.

13. The food product of claim 12, wherein the food product contains about 20% by weight more cocoa polyphenols.

14. The food product of claim 11, wherein the cocoa ingredient is selected from the group consisting of chocolate liquor, partially defatted or fully defatted cocoa solids, cocoa extract, a synthetic cocoa procyanidin or derivative thereof, and mixtures thereof.

15. The food product of claim 14, wherein the cocoa ingredient is the chocolate liquor or a mixture thereof with the partially or the fully defatted cocoa solids.

16. The food product of claim 11, wherein at least one of the cocoa ingredients is prepared from cocoa beans having a fermentation factor of less than 300.

17. The food product of claim 11, wherein the food product is a chocolate.

18. The food product of claim 17, wherein the chocolate is a dark chocolate.

19. The food product of claim 17, wherein the chocolate is a milk chocolate, a buttermilk chocolate, a skim milk chocolate, or a mixed dairy chocolate.

20. The food product of claim 17, wherein the chocolate is a reduced fat chocolate.

* * * * *